United States Patent [19]

Ward et al.

[11] Patent Number: 4,678,808
[45] Date of Patent: Jul. 7, 1987

[54] RAPID ACTING INTRAVENOUS EMULSIONS OF OMEGA-3 FATTY ACID ESTERS

[75] Inventors: Michael V. Ward, McHenry; Richard Cotter, Libertyville, both of Ill.

[73] Assignee: Baxter Travenol Laboratories, Inc., Deerfield, Ill.

[21] Appl. No.: 787,741

[22] Filed: Oct. 15, 1985

[51] Int. Cl.$^4$ .................... A61K 31/20; A61K 31/685
[52] U.S. Cl. ..................................... 514/560; 514/77; 514/78; 514/822
[58] Field of Search .................... 424/95; 514/560, 77, 514/78

[56] References Cited

U.S. PATENT DOCUMENTS 4,513,008  4/1985  Revici et al. ................... 514/560

OTHER PUBLICATIONS

Needleman, P. et al., "Triene Prostaglandins" Proc. Natl. Acad. Sci. 76(2): 944 ∝ 948, 1978.
Bang, H. et al., "The Composition of Food Consumed by Greenland Eskimos" Acta Med Scand. 200:69–73, 1976.
Sanders, T. et al., "A Comparison of the Influence on Plasma Lipids on & Platelet . . . " Bnt. J. Nut. 50:521,522, 1983.
Goodnight, S. et al., "The Effects of Dietary $\omega 3$ Fatty Acids . . . " Blood, 58(5): 880–885, 1981.
Thorngren, M. et al., "Effects of 11–Week Increase in Dietary Eicosapentaenoic Acid" the Lancet Nov. 1981, 1190.
Lorenz, R. et al., "Platelet Function . . . " Circulation 67(3):504–511, 1983.

Primary Examiner—Johnnie R. Brown
Assistant Examiner—John W. Rollins
Attorney, Agent, or Firm—Susan B. Fentress; Paul C. Flattery

[57] ABSTRACT

Described are lipid emulsions of marine oils comprising high concentrations of omega-3-fatty acid esters and low concentrations of free fatty acids for intraveneous administration for the treatment of thrombic disease states. More specifically, a lipid emulsion for parenternal use is provided comprising an emulsifier, water and a marine oil comprising an omega-3-fatty ester in which the concentration of the free fatty acid in the emulsion is below about 5 meq/l.

17 Claims, No Drawings

RAPID ACTING INTRAVENOUS EMULSIONS OF OMEGA-3 FATTY ACID ESTERS

BACKGROUND OF INVENTION

This invention relates to a therapeutic composition, methods for its preparation and for its use. More particularly, this invention relates to an emulsion of marine oil for treatment of thrombotic disease.

The therapeutic use of intravenous (IV) lipid emulsions in the clinically ill has its origin in antiquity. Physicians originally attempted infusions of olive oil and milk into the blood stream of critically ill patients in the 1600s and 1700s. The therapeutic reason for these infusions was to prevent starvation, often the deciding factor in the survival of such patients. Lipid is an attractive nutritional high calorie source (9kcal/g) as compared to carbohydrate (4kcal/g). These early experiments were unsuccessful due to severe adverse reactions. A long search for an appropriate lipid source for clinical nutrition ensued.

Various oil sources including butter oil, coconut oil, cottonseed oil, lard oil, olive oil, sesame seed oil, safflower oil and soybean oil, containing esters of fatty acids (6–22 carbons long) were tried. Also various emulsifying agents including soybean phosphatides, sorbitan monolaurate, polyglycerol esters of fatty acids, gelatin, cholesterol, sodium cholate and egg yolk phosphatides which are necessary to allow solubility of these lipids in an aqueous environment such as the blood stream were employed. (Thompson, S. W. The Pathology of Parenteral Nutrition with Lipids. Springfield, IL: Charles C. Thomas, 1974) This search was at first unsuccessful due to impurities such as high free fatty acids found in these primitive oils and emulsifiers. Over the last thirty years this search has focused on two possible oils and emulsifiers that showed therapeutic potential. The first of these were liquid emulsions composed of cottonseed oil (10 to 20% wt/v), soybean phospholipid (1–5% wt/v) and glycerin (2.25% w/v). Early emulsions of this composition showed a high degree of toxicity in both animals and man. (Meng, H. C. and J. S. Kaley., Effects of Multiple Infusions of a Fat Emulsion on Blood Coagulation, Liver Function, and Urinary Excretion or Steroids in Schizophrenic Patients. J Clin Nutr 16: 156–164, 1965) Since then such emulsions have undergone improvements. Both the oil and emulsifiers have been further characterized and purified and presently appear to provide a therapeutic modality to supply calories to the critically ill. (Lipofundin S. Fat Emulsion for Parenteral Hyperalimentation and Supply of Polyunsaturated Essential Fatty Acids. Germany: B. Braun, 1981) However, due to their notorious past, emulsions of such composition are little used in clinical nutrition.

The second emulsion which evolved during this period was one composed of purified soybean oil (10–20% wt/v), egg yolk phospholipids (1–5% wt/v) and 2.25% w/v glycerin. This emulsion, due to the purified nature of its components, produced clinically acceptable results as a calorie source in clinical nutrition. (Wrentlind, A. Current Status of Intralipid and other Fat Emulsions. pp109–122 in: Fat Emulsions in Parenteral Nutrition. Meng, H. C. and Wilmore, D. W., ed. Chicago, American Medical Association, 1976) This emulsion then established lipid emulsions as a viable nutrition therapy, and several emulsions of this composition are presently on the market. Recent additions to this family of lipid calorie sources are compositions of safflower oil and mixtures of soybean and safflower oils which appear to be viable emulsions as well. (Ament, M. E., R. A. Cannon, and W. J. Byrne. Use of Intravenous Safflower Oil Emulsion (Liposyn 10%) as an Energy Source in Pediatric Patients on TPN. (p165 in Parenteral Nutrition in the Infant Patient. North Chicago, IL: Abbott Laboratories, 1983)) From this historical summary it would appear that the nature of the oil and emulsifier appear to be less important than their purity for their use in clinical nutritions.

As the emulsions were developing, the biochemistry of lipids was also evolving. This resulted in the discovery of the biological essentiality of certain polyunsaturated fatty acids [linoleic acid (C18:2 omega 6), arachidonic acid (C20:4 omega 6)]. (Holman, R. T. How Essential are Essential Fatty Acids. J Amer Oil Chem Soc, 55: 744A-781A, 1978) It was observed that lack of these essential fatty acids produced a clinical syndrome characterized by scaliness and lesions of skin, cessation of growth, renal degeneration, structural and metabolic changes in the central nervous system, increased metabolic rate, weight loss and finally death. (Caldwell, M. D. Human Essential Fatty Acid Deficiency: A Review in Fat Emulsions in Parenteral Nutrition. Meng, H. C. and Wilmore, D. W., eds. Chicago, IL: Amer Med Assoc, p24, 1978) More recently, the essentiality of linolenic acid (C 18:2 omega 3) has been postulated. Deficiencies in this fatty acid cause optical and neurological disturbances. (Neuringer, M., W. E. Connor, C. Van Patten, and L. Bostad. Dietary Omega 3 Fatty Acid Deficiency and Visual Loss in Infant Rhesus Monkeys. J Clin Chem 73: 272–276, 1984). These developments further increased the therapeutic utility of lipids in clinical nutrition.

The fat emulsions outlined above have been used successfully both as a calorie and an essential fatty acid source for the last twenty years. (Pelham, D. Rational Use of Fat Emulsions. The Hosp Pharm Forum 10:1, 1981) Problems associated with their use are generally considered to be due to lipid overload. This is when concentrations of lipid in the emulsion or its metabolic products (free fatty acids) are such that the body is unable to metabolize them. (Alexander, C. S. Fat infusions: Toxic Effects and Alterations in Fasting Serum Lipids following Prolonged Use. Arch Intern Med 107: 94–514, 1961) This results in lipid accumulation in various cells, tissued, and organs of the body. (Belin, R. P., B. A. Bivins, J. Z. Jona, V. L. Young. Fat Overload with a 10% Soybean Oil Emulsion. Arch Surg 111: 1391, 1976) High levels in the blood of the emulsion's by-products, free fatty acids, have been shown to cause both cardiac and lung damage. (Soloff, L. A. Arrhythmias Following Infusions of Fatty Acids. Amer Heart J 80: 671, 1970; Broe, P. J., T. J. K. Toung, S. Margolis, S. Permutt and J. L. Cameron. Pulmonary Injury Caused by Free Fatty Acid. Evaluation of steroid and albumin therapy. Surgery 89: 582, 1981)

Fat emulsions are recommended clinically to be used at dosages of 2.5 g/kg/24 hours for adults and up to 4 g/kg/24 hours for children. (TRAVAMULSION 10% I.V. fat emulsion product insert. Deerfield, IL: Travenol Laboratories, 1985) These emulsions contain no more than 5 meq/liter of free fatty acids. The dosage level of these emulsions are recommendations and each patient must be monitored for the build up of emulsions and free fatty acids during infusion to assure safety of such therapies. Extensive studies to assess the metabolism and pharmacokinetics of these emulsions during infusion have been conducted and are well understood at this time. (Cotter, R., L. Martis, F. Cosmas, H. Sargent, C. Taylor, W. Remis, S. Young, W. B. Rowe, and E. Woods. Nonlinear kinetic analysis of the elimination of lipid emulsion administered Intravenously to Dogs. J Paren Ent Nutr (7(3): 244–250, 1983; Cotter, R., L. Martis, F. Cosmas, H. Sargent, C. Taylor, S. Young, W. B. Rowe, and E. Woods. Comparison of the Elimination and Metabolism of 10% TRAVAMULSION and 10% Intralipid Lipid Emulsion in the Dog. J Paren Ent Nutr 8(2): 140–145, 1984; Cotter, R. L. Martis, F. Cosmas, C. Taylor, S. Young, W. B. Rowe, and R. Johnson. Comparison of the Elimination of 10 and 20% TRAVAMULSION Lipid Emulsion from the Blood of Beagle Dogs. Amer J. Clin Nutr 41(5): 994–1001, 1985)

Presently a new generation of lipid emulsions is under development. These emulsions are designed as therapeutic modalities for clinical conditions that have high metabolic energy requirements. These conditions are a result of hormonal and biochemical aberrations that alter normal energy metabolism and shift it into a hypermetabolic state. (Raymond, R., R. Cotter, F. Cosmas, and D. Gibbons. Development of a Chronic Peritoneal Abscess Model in the Dog from Evaluation of Clinical Therapies. Fed Proc 43: 325, 1984) Such states are found in critically ill patients suffering from trauma, sepsis and burns. (Kinney, J. M. and P. Felig. The Metabolic Response to Injury and Infection. Endocrinology 3: 1963, 1979) These emulsions are composed of medium chain fatty acids (C6 to C12) esterified to glycerol to form medium chain triglycerides which are emulsified with (1–5% wt/v) egg yolk phospholipids to give a final triglyceride concentration of 10 to 20% wt/v. (Cotter, R., F. Cosmas, R. Johnson, B. Rowe, and L. Lin. A Comparison of the Elimination of Four Different Formulations of Parenteral Lipid Emulsions from the Blood Streams of the Beagle Dog. Fed Proc 44: 1146, 1985) These emulsions are of benefit in the hypermetabolic state as they supply twice as much metabolic energy per gram of lipid at a faster rate due to their unique biochemical advantage of carnitine independence, rapid betaoxidation and lack of deposition in organs and adipose tissue as compared to long chain triglycerides (C12–C24). (Cotter, R. C. Johnson, C. A. Taylor, T. Pavline, F. Cosmas, and W. B. Rowe. Metabolic Comparison of a 20% Combination Long and Medium Chain Triglyceride Lipid Emulsion and a 20% Long Chain Emulsion. Fed Proc 43: 848, 1984; Johnson, R. C., S. K. Young, R. Cotter, and W. B. Rowe. Metabolism and Distribution of Medium Chain Triglyceride Lipid Emulsion. Amer J. Clin Nutr 41: 846, 1985) Extensive research has been carried out to develop and characterize these emulsions, illustrating their metabolic advantage. (Young, S. K., R. C. Johnson, R. Cotter, and B. Rowe. Competitive Interaction Between Medium and Long Chain Lipid Emulsions. Fed Proc 43: 865, 1984).

The rapid bioavailability of lipid emulsions creates immediate biological effects and makes them attractive vehicles for acute intravenous therapies. Further studies have also shown that by reducing the phospholipid composition of the emulsion to about 0.4–0.6% a more rapid bioavailability is produced. This rapid bioavailability is produced by creating a more attractive lipid particle for apolipoprotein transfer from high density lipoproteins found in circulating blood. Such apolipoproteins are essential for control of lipid emulsion endothelial receptor binding and activation of hydrolytic enzymes at these receptor sites. The reduction in phospholipids in such emulsions results in a more rapid delivery of the emulsion to metabolism and a release of the biologically active metabolic products. This brings about a rapid biological response to these therapies.

Lipid emulsions containing marine oil have been proposed for the treatment of disorders associated with imbalances of arachidonic acid metabolites. Examples include: autoimmune syndromes; acute and chronic inflammatory diseases such as psoriasis and acute respiratory distress syndrome (ARDS); atherosclerosis, stroke, myocardial infarction, deep vein thrombosis and other cardiovascular diseases. The most notable cardiovascular risk factors include surgery, hyperlipidemic states, hypertension (stroke), enhanced platelet responsiveness, vascular lesions and occlusions, vascular spasm and diabetes. Studies have shown that populations (Greenland Eskimos) whose diets are rich in marine products are at considerably reduced risk of developing coronary heart disease. (Editorial. Eskimo diets and diseases. Lancet: 1139–1141, May 21, 1983) Such diets are rich in fatty acids of the omega three (omega 3) family. The three members of this family which appear to play a significant role in this effect are linolenic acid (C18:3), eicosapentaenoic acid or EPA (C20:5), and docosahexaenoic acid or DHA (C22:6).(Bang, H. O., J. Dyerberg, and N. Hjorne. The Composition of Food Consumed by Greenland Eskimos. Acta Med Scand 200: 69–73, 1976)

In the average European and North American diet, linoleic acid (C18:2), an omega 6 fatty acid, is the predominantly consumed essential fatty acid, accompanied by low levels of linolenic acid. Linoleic acid is converted to arachidonic acid (C20:4), both of which are incorporated into the lipid component of cell membranes and serum, and give rise to metabolites of the omega 6 pathways.

Cold water marine animals contain low concentrations of the essential fatty acid, linolenic, in their tissues and large amount of two other members of the omega 3 family: EPA and DHA. These fatty acids are also incorporated into cell membranes and serum and give rise to metabolites of the omega 3 pathways. The two metabolic pathways containing the omega 3 fatty acids are not interchangeable in animals. However, the enzymes which metabolize the omega 6 and omega 3 series seem to be identical.

Most animal cells utilize these fatty acids to form various prostaglandins and leukotrienes. (Spector, A. A., T. L. Kuduce, P. H. Figard, K. C. Norton, J. C. Hoak, and R. L. Czeruionke. Eicosapentaenoic Acid and Prostacyclin Production by Cultured Human Endothelial Cells. J Lipid Res 24: 1595–1604, 1983; Lee, T. H., R. L. Hoover, J. D. Williams, et al. Effect of Dietary Enrichment with Eicosapentaenoic and Docosahexaenoic Acids on in vitro Neutrophil and Monocyte Leukotriene Generation and Neutrophil Function. N Engl J Med 312(19): 1217–1224, May 9, 1985) When fatty acids are released from cell membranes and intracellular pools, the lipoxygenase and cyclooxygenase enzymes mediate the production of various eicosanoids. Although EPA is a relatively poor substrate for cyclooxygenase, it appears to have a high binding affinity and thereby inhibits arachidonic acid conversion by this enzyme. (Needleman, P., A. Raz, M. Minkes, J. A. Ferrendelli, and H. Sprecher. Triene Prostaglandins, Prostacyclin and Thromboxane Biosynthesis and Unique Biological Properties. Proc Nat Acad Sci USA 76: 944, 1979) On the other hand, EPA is a good substrate for the lipoxygenase enzymes. (Terano, T., J. A. Salmon, and S. Moncada. Biosynthesis and biological activity of leukotriene $B_5$. Prostaglandins 27(2): 217-232, 1984) In either case, EPA would have clinical application in disorders associated with elevated levels of arachidonic acid metabolites (examples: thromboxane $B_2$ mediated myocardial infarction; (Hay, C. R. M., A. P. Durber, and R. Saynor. Effect of Fish Oil on Platelet Kinetics in Patients with Ischemic Heart Disease. Lancet 1269-1272, June 5, 1982) and leukotrienes in psoriasis. (Brain, S. D., R. D. R. Camp, A. Kobza Black, et al. Leukotrienes $C_4$ and $D_4$ in psoriatic skin lesions. Prostaglandins 29(4): 611-619, 1985)

An additional application of the omega 3 fatty acid pathway lies in the physiological activities of their cellular products. EPA has been shown to lower platelet activity. (Holme, S., J. H. Brox, H. Krane, and A. Nordoy. The Effect of Albumin Bound Polyunsaturated Fatty Acids on Human Platelets. Throm Haemostas 51(1): 32-36, Stuttgart, 1984) Platelet activation and release is implicated in the pathophysiology of such cardiovascular disorders as atherosclerosis; (Ross, R., and L. Harker, Hyperlipidaemia and atherosclerosis. Science 193: 1094, 1976); thrombosis, (Hornstra, G. Dietary Fats and Arterial Thrombosis: Effects and Mechanism of Action. Prog Biochem Pharmacol 14: 326-338, 1977); myocardial infarction, (Hay, C. R. M., A. P. Durber, and R. Saynor, Effect of Fish Oil on Platelet Kinetics in Patients with Ischemic Heart Disease, Lancet 1269-1272, June 5, 1982); and shock. (Lefer, A. M. Role of the Prostaglandin-Thromboxane System in Vascular Homeostasis During Shock. Circ Shock G: 297-303, 1979)

Many short-term studies involving the daily administration of some marine products to apparently health human subjects have demonstrated similar findings to those reported for Greenland Eskimos. There is a mild bleeding defect (prolonged bleeding time) and platelet aggregation response to collagen, or ADP is markedly reduced. (Goodnight, S. J., W. C. Harris, and W. E. Connor. The Effects of Dietary Omega-3 Fatty Acids on Platelet Composition and Function in Man: A Prospective, Controlled Study. Blood 58(5): 880-885, 1981; Thorngren, M., and A. Gustafson. Effects of 11-week Increase in Dietary Eicosapentaenoic Acid on Bleeding Time, Lipids, and Platelet Aggregation. Lancet: 1190-1193, Nov 28, 1981) In nonhuman primates with advanced atherosclerosis and markedly shortened platelet survival times, the offering of a diet containing EPA resulted in the normalizing of platelet survival times. (Ward, M. V., and T. B. Clarkson. The Effect of a Menhaden Oil Containing Diet on Hemostatic and Lipid Parameters of Nonhuman Primates with Atherosclerosis. Atherosclerosis (in press))

In most normal subjects and patients who consume such diets, total serum cholesterol, very low density lipoprotein cholesterol, and triglycerides are significantly lowered. (Mortensen, J. Z., E. B. Schmidt, A. H. Nielsen, and J. Dyerberg. The Effect of N-6 and N-3 Polyunsaturated Fatty Acids on Hemostasis, Blood Lipids and Blood Pressure. Thromb Haemostas 50(2): 543-546, Stuttgart, 1983; Phillipson, B. E., D. W. Rothrock, W. E. Connor, W. C. Harris, and D. R. Illingworth. Reduction of Plasma Lipids, Lipoproteins, and Apoproteins by Dietary Fish Oils in Patients with Hypertriglyceridemia. N Engl J Med 312(19): 1210-1216, 1985) High density lipoproteins (HDL) cholesterol concentrations may be elevated in some subjects. (Sanders, T. A. B., and M. C. Hochland. A Comparison of the Influence on Plasma Lipids and Platelet Function of Supplements of Omega-3 and Omega-6 Polyunsaturated Fatty Acids. Brit J Nutr 50: 521-529, 1983) This pattern of change would be one thought to be less atherogenic.

Studies with animals have shown that those fed diets containing EPA, as opposed to commercial chows, have significantly lower infarct sizes when their coronary or carotid arteries are ligated. (Culp, B. R., W. E. M. Lands, B. R. Lucchesi, B. Pitt, and J. Romson. The Effect of Dietary Supplementation of Fish Oil on Experimental Myocardial Infarction. Prostaglandins 20(6): 1021-1031, 1980; Black, K. L., B. Culp, D. Madison, O. S. Randall, and W. E. M. Lands. The Protective effects of dietary fish oil on focal cerebral infarction. Prostaglandins & Med 3: 257-268, 1979). The difference is thought to be due to a reduced oxygen demand on the part of the affected tissue. This would support the findings from studies with nonhuman primates whereby a diet containing EPA had a sparing effect upon the onset and extent of myocardial ischemia after isoproterenol stress tests. (Ward, M. W. Unpublished finding, Bowman Gray School of Medicine, Winston-Salem, NC) In studies with human subjects fed marine products, both blood pressure and blood pressure response to norepinephrine fell significantly. (Lorenz, R., U. Spengler, S. Fischer, J. Duhm, and P. C. Weber. Platelet Function, Thromboxane Formation and Blood Pressure Control During Supplementation of the Western Diet with Cod Liver Oil. Circulation 67(3): 504-511, 1983).

Change in fatty acid composition of blood cell membranes and serum may explain some of the aforementioned physiological observations. With the ingestion of a marine diet, the omega 3 fatty acids increase markedly at the expense of the omega 6 fatty acids.

There may even be other benefits to fish products. Certain mice that die at an early age of autoimmune disease have been given prostaglandin $E_1$ ($PGE_1$) or menhaden oil diets and exhibited markedly longer lifespans and a virtual disappearance of immune mediated glomerulonephritis. (Kelley, V. E., A. Winkelstein, S. Isui, and F. J. Dixon. Prostaglandin $E_1$ Inhibits T-Cell Proliferation and Renal Disease in MRL/1 Mice. Clin Immunology & Immunopathology 21: 190-203, 1981; Prickett, J. D., D. R. Robinson, and A. D. Steinberg. Dietary Enrichment with the Polyunsaturated Fatty Acid Eicosapentaenoic Acid Prevents Proteinuria and Prolongs Survival in NZB X NZW $F_1$ Mice. J Clin Invest 68: 556-559, 1981) Fish oil was also found to be beneficial in a marine model of anyloidosis. (Hayes, K. D., E. Cathcart, C. A. Leslie, and S. N. Meydani. Dietary Fish Oil Alters Prostaglandin Metabolism to Decrease Platelet Aggregation in Monkeys and Anyloidosis in Mice. Proc of Conf on Omega-3 Fatty Acids. Reading, England: Reading University, 131-132, Jul 16-18, 1984).

The beneficial effects of fish oils in inflammatory disorders stem, at least in part, from the interaction of EPA and arachidonic acid with the enzyme lipoxygenase in inflammatory cells (neutrophils and monocytes). In the presence of EPA these cells produce less Leukotriene $B_4$ (a major component of inflammatory response) and small amounts of Leukotriene $B_5$. (Lee, T. H., R. L. Hoover, J. D. Williams, et al. Effect of Dietary Enrichment with Eicosapentaenoic and Docosahexaenoic Acids on in vitro Neutrophil and Monocyte Leukotriene Generation and Neutrophil Function. N Engl J. Med 312(19): 1217-1224, 1985) $LTB_5$ is at least 30 times less potent than $LTB_4$ in causing aggregation, chemokinesis and degranulation of human neutrophils in vitro. The potency of $LTB_5$ in potentiating bradykinin-induced plasma exudation, which is probably attributable to its leukotactic activity, is as least 10 times lower than that of $LTB_4$. (Terano, T., J. A. Salmon, and S. Moncada. Biosynthesis and Biological Activity of Leukotriene $B_5$. Prostaglandins 27(2): 217-232, 1984)

U.K. patent application GB No. 2 139 889A discloses an emulsion for intravenous use which contains a fatty acid containing 20-22 carbon atoms or an ester of the fatty acid, a vegetable oil, an emulsifier and water.

It is an object of this invention to provide a lipid emulsion for intravenous therapy and treatment of thrombotic disease. It is a further object of this invention to provide an emulsion which inhibits formation of certain prostaglandins. It is a further object of this invention to provide such an emulsion wherein the concentrations of free fatty acids are below toxic levels.

Other objects appear hereinafter.

SUMMARY

We have found that lipid emulsions of marine oils comprising high concentrations of omega-3-fatty acid esters and low concentrations of free fatty acids are therapeutic when administered intravenously for the treatment of thrombotic disease states.

Specifically, a lipid emulsion for parenteral use is provided comprising an emulsifier, water, and a marine oil comprising an omega-3 fatty acid ester, in which the concentration of free fatty acid in the emulsion is below about 5 meq/l. Preferably, the concentration of marine oil in the emulsion is between 5 and 50% (wt/v).

Specifically, marine oil containing omega-3 fatty acid esters is predominantly made of acids of 12-26 carbon atoms each, for example, esters of eicosapentaenoic acid (EPA) and docosahexaenoic acid (DHA), typically as a mixture, although pure species may be used as well. Preferably, the ester of EPA may be present in the marine oil in a concentration of 10 to 100% by weight.

Typical esters of EPA, DHA, or other unsaturated acids of 12-26 carbons are the glyceryl esters of naturally occurring fats.

The emulsifier may be any physiologically appropriate emulsifier, being typically selected from the group consisting of egg yolk phosphatide, soy phosphatide, purified egg yolk lecithin, purified soy lecithin, and other purified phospholipids. The emulsifier concentration may typically range from 0.2 to 1.5%, and preferably about 0.3 to 0.8% for optimum production of rapid bioavailability of EPA and DHA.

The term "omega-3 fatty acid ester" is defined to mean that the particular fatty acid included in the ester has a double bond occuring at the third position from the methyl end of the fatty acid. Likewise, the term "omega-6" implies that the first double bond in the molecule of the fatty acid in question occurs at the sixth position from the methyl end.

Preferably the lipid emulsions of this invention are free of vegetable oils and acids derived therefrom.

DETAILED DESCRIPTION OF THE INVENTION

All percentages in this application refer to weight/volume unless otherwise noted.

The intravenous lipid emulsions of this invention comprise marine oil, an emulsifier, and water.

The marine oils to be used herein are those which are preferably highly purified. These oils have a high concentration of fatty acid esters relative to free fatty acids. Examples of such oils include:
  menhaden oil,
  salmon oil,
  sardine oil,
  and other fish oils from cold water ocean fish.

The amount of oil to be used in the emulsion will depend upon the dosage, the percentage of fatty acid esters in the oil, and the total lipid concentration of the emulsion. Therapeutic dosages will be dependent upon body weight and infusion duration. The omega 3 fatty acid ester content of the oil will also vary depending upon the oil source. Concentrations will range from 10 to 100% and preferably at least 30%. Free fatty acid concentration of total lipid emulsion should be below 5 meq/l. Concentration of the marine oil in the emulsion will vary between 5 to 50%. Preferred concentrations are between 10 to 20%; concentrations of emulsifiers will vary accordingly.

Emulsifiers which are useful in this invention include egg yolk phosphatide, soybean phosphatide, egg yolk lecithin, soybean lecithin and other purified phospholipids. Concentrations of the emulsifiers are dependent upon the amount of oil in the emulsion. Concentrations may range from 0.1 to 6%. For each additional 10% increase in oil, emulsifier concentration will increase approximately 0.4 to 1.2%. Preferred concentrations are about 0.4 to 1.2% where volume of oil is between 10 to 20%.

Various osmotic agents may also be added to the emulsion. Examples of such osmotic agents include glycerin, glucose, sucrose, sorbitol, protein and sodium acid phosphates. The osmolarity of this solution preferably ranges between 280 to 300 milliosmoles. The remainder of the emulsion comprises mostly water and other optional additives.

The lipid particles in the emulsion will have a diameter of less than about 0.75 μm and preferably less than about 0.5 μm. The emulsions will be sterile and ordinarily are packaged in glass or plastic containers. They can be made by known methods. For example, see U.S. Pat. No. 3,169,094 and European Patent Application No. 0071995. The emulsions herein are packaged and stored in hermetically sealed containers for long and short-term storage.

EXAMPLE 1

In a suitable vessel, 1.0 to 2.0 Kg of marine oil containing 15-30% glycerol ester of eicosapentaenoic acid (EPA) and 15-25% glycerol ester of docosahexaenoic acid (DHA), 120 g of purified egg phospholipids, 225 g of glycerol, USP, (as an osmotic agent) and water for injection USP are mixed to produce an emulsion having a 2.25% glycerol concentration and a 10 to 20% marine oil concentration. This emulsion is then homogenized repeatedly at high pressure to produce an emulsion of mean particle diameter of less than 0.75 μm. During the process, the pH of the emulsion is adjusted to a physiological range with sodium hydroxide. The final volume is adjusted, if necessary with water for injection, USP, to 10 liters, and the emulsion is filtered into glass containers and heat sterilized by the normal procedure.

EXAMPLE II

A 10% lipid emulsion of the type of Example 1 was administered, via a cephalic vein intravenously, to each of 6 dogs, continuously over an 8 hour period, at a rate of 40 mg EPA/kg/hr (2.5 ml/kg/hr). Each of the same 6 dogs received similar 8 hour infusions of Liposyn 10% Safflower oil lipid emulsion (Abbott Laboratories, North Chicago) and physiological saline (Travenol) in equivalent volumes to those administered for the Example 1 lipid emulsion (2.5 ml/kg/hr). There was a 21 day washout period between each infusion to the same dog. The order of treatments was randomized.

The Example 1 lipid emulsion contained 10 gm marine oil per 100 ml emulsion, and 16.42 mg EPA per ml of emulsion. From the time of production until the time of infusion, the Example 1 lipid emulsion was stored at approximately 4° C. During the infusion, the emulsion stood at room temperature.

Citrated whole blood samples were drawn from each dog at the following times: pre-infusion, and 2, 4, 6, 8, 10, 24, and 48 hours following the start of infusion. Assays completed with these blood samples included whole blood platelet aggregation to adenine-5-diphosphate (ADP) and collagen, prothrombin time, and activated partial thromboplastin time. Whole blood platelet counts were also measured at the above listed time periods, using whole blood collected into EDTA.

After the administration of the Example 1 lipid emulsion, dog platelets challenged with 8 µM adenine-5-diphosphate (ADP) were inhibited 80%, 29.8% and 21% at 8, 24, and 48 hours after beginning infusion, respectively, when compared to pre-infusion responses. When these same platelets were challenged with 2 µg/ml of acid soluble collagen, they were inhibited 72.9%, 25.8% and 20% at 8, 24, and 48 hours after beginning infusion, respectively, when compared to pre-infusion responses. After the administration of Liposyn, dog platelet responses to both ADP and collagen were at or above (hyperactive) pre-infusion values at both 24 and 48 hours after beginning infusion. Platelet counts were unaltered by the infusion of the Example 1 lipid emulsion, Liposyn, or saline.

A cuticle bleeding time test was used in this dog study. This is an "open bleed" assessment of hemostatic capacity in which a toenail is severed in a manner sufficient to transect the vascular supply to that nail. The test measures the length of time required to cease bleeding. These tests were completed on each dog pre-infusion, and at 8 and 24 hours after beginning infusion. Cuticle bleeding times of dogs receiving the Example 1 lipid emulsion were increased 158% and 152% above pre-infusion values at the 8 and 24 hour time periods, respectively. These increases were consistent with the inhibition of platelet function. Dogs receiving Liposyn had bleeding times decrease 14% and 22% below pre-infusion values at the 8 and 24 hours time periods, respectively. These decreases were consistent with the platelet aggregation responses at the same time periods.

Blood coagulation tests revealed significant prolongations of both prothrombin times and activated partial thromboplastin times with blood samples collected from dogs receiving the Example 1 lipid emulsion. These changes were not seen with the infusion of saline or Liposyn.

EXAMPLE III

A 10% lipid emulsion made as in Example 1 was administered, via a saphenous vein intravenously, to each of 6 African Green Monkeys, continuously over a six hour period, at a rate of 125 mg EPA/kg/hr (5 ml/kg/hr). Each of the same six monkeys received similar six hour infusions of 10% lipid emulsion containing soybean oil (TRAVAMULSION ®, Travenol Laboratories, Inc.) in equivalent volumes to those administered for the EPA lipid emulsion (5 ml/kg/hr). There was a twenty-one day washout period between each infusion in the same monkey.

The Example 1 lipid emulsion contained 10 gm of marine oil per 100 ml emulsion, and 25 mg EPA/ml of emulsion. From the time of production until the time of infusion, the Example 1 lipid emulsion was stored at approximately 4° C. During the infusion, the emulsion stood at room temperature.

Citrated whole blood samples were drawn from each monkey pre-infusion, and at 6, 12, and 24 hours after beginning infusion. These samples were used to measure whole blood platelet aggregation to acid soluble collagen, and thromboxane $B_2$ release by platelets after platelet aggregation to collagen. Whole blood platelet counts were also measured at the above-listed time periods, using whole blood collected into EDTA.

Platelet counts remained unchanged for both treatments. The Example 1 lipid emulsion and TRAVAMULSION ® lipid emulsion were comparable in effect 6 hours after beginning infusion, when comparing platelet aggregation responses and thromboxane $B_2$ release values. EPA lipid emulsion was significantly more effective than TRAVAMULSION ® lipid emulsion in reducing platelet function at both 12 and 24 hours after beginning infusion. The following is a summary of those responses:

Percent of Pre-infusion African Green Monkey Platelet Function After Intravenous Lipid Emulsion

| Collagen | Hours after beginning infusion | EPA lipid emulsion | | TRAVAMULSION | |
|---|---|---|---|---|---|
| | | platelet aggregation | thromboxane release | platelet aggregation | thromboxane release |
| 1 µg/ml Collagen | 6 | 22.5% | 45.7% | 60.9% | 50.7% |
| | 12 | 14.5 | 22.8 | 77.4 | 57.3 |
| | 24 | 25.1 | 40.2 | 109.6 | 99.9 |
| 2 µg/ml Collagen | 6 | 53.4 | 51.7 | 86.9 | 40.3 |
| | 12 | 30.5 | 30.6 | 108.3 | 59.0 |
| | 24 | 45.0 | 46.1 | 123.2 | 98.0 |

We claim:

1. A lipid emulsion for parenteral use comprising an emulsifier, water and a marine oil comprising at least one omega 3 fatty acid ester wherein the concentration of free fatty acid in the emulsion is below about 5 meq/l and wherein the concentration of marine oil is between about 5% to about 50%.

2. The emulsion of claim 1 wherein the marine oil contains at least 30% by weight of a combination of esters of eicosapentaenoic acid and docosahexaenoic acid.

3. The emulsion of claim 1 wherein the concentration of the ester of eicosapentaenoic acid in the marine oil is between about 10% to about 100%.

4. The emulsion of claim 1 wherein the emulsifier is selected from the group consisting of egg yolk phosphatide, soy phosphatide, purified egg yolk lecithin, purified soy lecithin and other purified phospholipids.

5. The emulsion of claim 1 wherein the emulsifier concentration is either 1.2%, 0.6% or 0.4%, the latter two being the most effective in producing rapid bioavailability of eicosapentaenoic acid and docosahexaenoic acid.

6. The emulsion of claim 6 wherein the osmotic agent is selected from the group containing glycerin, glucose and sucrose, sorbitol, physiologically aceptable sodium phosphate.

7. The emulsion of claim 1 further comprising an osmotic agent.

8. The emulsion of claim 1 in which essentially all lipid particles present have a diameter of less than 0.5 microns.

9. The emulsion of claim 1 having an osmolarity of 280 to 300 milliosmoles.

10. The emulsion of claim 1 wherein the marine oil is selected from the group comprising menhaden oil, salmon oil and sardine oil.

11. A lipid emulsion for intravenous administration use and effective for inhibiting platelet function comprising from 0.2 to 1.5% of an emulsifier selected from the group consisting of egg yolk phosphatide, soy phosphatide, purified egg yolk lecithin, and purified soil lecithin, from 5 to 50% of a marine oil comprising at least 30% of omega-3 fatty acid esters of glycerol, and water, essentially all lipid particles in the emulsion having a diameter of less than 0.75 microns.

12. The lipid emulsion of claim 11 in which the marine oil contains at least 30% by weight of a combination of glycerol esters of eicosapentaenoic acid and docosahexaenoic acid.

13. The lipid emulsion of claim 12 in which the concentration of marine oil present is from 10 to 20%.

14. The lipid emulsion of claim 13 in which an osmotic agent is present selected from the group consisting of glycerin, glucose, sucrose, sorbitol, physiologically acceptable proteins, and sodium acid phosphate.

15. The lipid emulsion of claim 14 in which sufficient osmotic agent is present to provide an osmolarity of 280 to 300 milliosmoles.

16. The lipid emulsion of claim 15 in which less than 5 meq/l of free fatty acids are present.

17. A method of rapidly inhibiting platelet function in an animal said method comprising intravenously administering to said animal a platelet inhibiting effective amount of a lipid emulsion comprising an emulsifier, water and a marine oil comprising at least one omega-3 fatty ester wherein the concentration of free fatty acid in the emulsion is below about 5 meq/l.

* * * * *